United States Patent [19]

Yoshida et al.

[11] Patent Number: 5,023,026
[45] Date of Patent: Jun. 11, 1991

[54] METHOD FOR HYDROPHILICATION TREATMENT OF SYNTHETIC RESIN OBJECT, AND CULTURE DEVICES AN INSPECTION APPARATUS TREATED BY SAME

[75] Inventors: Takao Yoshida, Tama; Keinosuke Isono, Kawaguchi; Tatsuo Suzuki, Machida, all of Japan

[73] Assignee: Material Engineering Technology Laboratory, Incorporated, Tokyo, Japan

[21] Appl. No.: 425,359

[22] Filed: Oct. 23, 1989

Related U.S. Application Data

[63] Continuation of Ser. No. 133,426, Dec. 15, 1987, abandoned.

[30] Foreign Application Priority Data

Dec. 17, 1986 [JP] Japan .................. 61-301035

[51] Int. Cl.⁵ .................................................. B29C 71/04
[52] U.S. Cl. ............................................ 264/22; 264/25
[58] Field of Search ..................... 264/22, 25, 132; 425/174.4; 427/44

[56] References Cited

U.S. PATENT DOCUMENTS

| | | | |
|---|---|---|---|
| 4,247,496 | 1/1981 | Kawckami et al. | 264/22 |
| 4,321,117 | 3/1982 | Kaetsu et al. | 522/129 X |
| 4,631,155 | 12/1986 | Caines | 264/22 |
| 4,726,928 | 2/1988 | Ejk et al. | 422/22 |
| 4,933,123 | 6/1990 | Yoshida et al. | 264/22 |

Primary Examiner—Michael Lusignan
Attorney, Agent, or Firm—Oblon, Spivak, McClelland, Maier & Neustadt

[57] ABSTRACT

Surface of synthetic resin object is hydrophilicated by irradiation of ultraviolet rays.

5 Claims, 1 Drawing Sheet

METHOD FOR HYDROPHILICATION TREATMENT OF SYNTHETIC RESIN OBJECT, AND CULTURE DEVICES AN INSPECTION APPARATUS TREATED BY SAME

This application is a continuation of application Ser. No. 07/133,426, filed on Dec. 15, 1987, now abandoned.

BACKGROUND OF THE INVENTION

(1) Field of the Invention

This present invention relates to a treatment method for the hydrophilication of synthetic resin object. This invention also relates to a hydrophilication treatment method by lowering a contact angle of the surface of synthetic resin object with water.

The present invention further relates to culture devices or inspection apparatus such as vessels for tissue culture and microorganism incubation. More particularly, it relates to the culture devices such as vessels for tissue culture and microorganism incubation or inspection apparatus and manufacturing method of the same by lowering the contact angle with water or an aqueous solution (hereinafter referred to as water) on the surface of aforesaid devices and apparatus with water.

This invention uses inexpensive equipment, dry treatment method and a simple process, and continuously provides various synthetic resin devices having uniformly treated surfaces, for example, dishes, bottles, slide and cover glasses, pipettes, diluter tips and further measuring vessels for general purpose.

(2) Description of the Prior Art

Tissue culture vessels represented by dishes, trays and bottles for the tissue culture cannot plate cells to be cultured on the vessel surface unless the contact surface of the above vessels with a medium is hydrophilic. Therefore conventional vessels are unsuitable for observing the growing conditions of afore-mentioned cells, morphology of each cellular body etc. The hydrophilication treatment of these vessels by some measure has been required. Various methods have traditionally been employed for the hydrophilication and they are substantially classified into the following three groups. One of the methods is to oxidize the resin surface by treating the resin vessels with a chromic acid mixture. Although this method of treatement is quite effective, death of cells sometimes occurs during the culture when the removal of the chromic acid mixture is unsatisfactory. Chromic acid mixture is also required to be disposed after complete neutralization because the acid causes public hazard problems by the disposal after use. In addition to such problems of waste liquid treatment, the manufacture by this method depends upon a batch process, is difficult to carry out by a continuous process and results in an increased production cost. Therefore this method has many problems.

On the other hand, a method for hydrophilicating the resin surface by coating with a hydrophilic resin has recently been developed. As the hydrophilic resin for use in this method, 2-hydroxyethyl methacrylate is applied on the surface after diluting with solvents. A method has also been reported wherein methyl methacrylate is applied and successively hydrolyzed with lactic acid. The method for coating the hydrophilic resin, however, has problems on the adhesion to vessels with the hydrophilic resin. The hydrophilic resin is apt to flake off from the vessels during use and there are many cases which are difficult to adapt to practical application. Even though flaking does not occur, a drying step is required after coating. It is very difficult to uniformly coat on the vessel surface depending upon the drying method and the resulting products have also problems on the with uniformity.

In addition, there is a method for imparting to the vessel a surface hydrophilic property by plasma etching with a plasma generator. In this method, the plasma generator is expensive. Furthermore the plasma etching requires removal or exchange of the gas in the equipment, takes much time for conducting the treatment and has disadvantage of low manufacturing efficiency and high treatment cost due to the batch process.

(4) BRIEF SUMMARY OF THE INVENTION

As mentioned above, problems were found with the conventional hydrophilication treatment method for synthetic resin surface of the culture devices and inspection apparatus as well as the hydrophilicated culture devices and inspection apparatus. Such problems include the stabilization of product performance, the disposal of waste liquid, the uniformity of treated surfaces, the complication of treatment step and the cost of treatment.

The purpose of this invention is to solve aforesaid problems and to provide a method for the hydrophilication treatment of synthetic resin which can continuously, easily and uniformly hydrophilicating the synthetic resin surface with an inexpensive equipment.

That is, the present inventors have extensively invetigated the method for the hydrophilication treatment of synthetic resin surfaces which can be continuously and easily carried out to obtain good uniformity of the treatment with a low production cost. As a result, traditional problems have been solved by providing a method for conducting an oxidation treatment of afore-mentioned synthetic resin surface with irradiation of ultraviolet rays.

(5) BRIEF DESCRIPTION OF THE DRAWINGS

Figure 1:
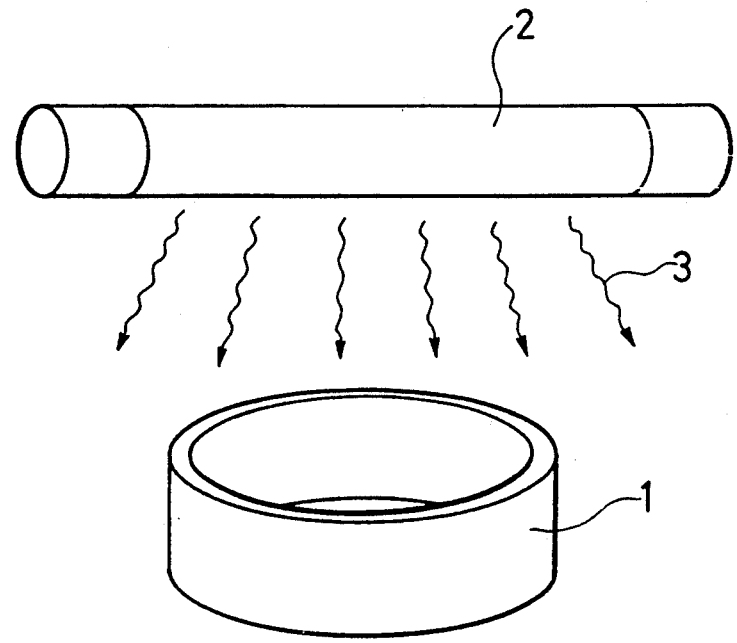
FIG. 1 is a perspective view illustrating an example of the method for conducting the hydrophilication treatment of synthetic resin surface in this invention.

In the drawings, the following numbers illustrate respectively:

| 1 molded article | 2 ultraviolet lamp |
| 3 ultraviolet rays | 4 oxygen |
| 5 ozone | 6 activated oxygen |
| 7 hydrogen | 8 resin surface |
| 9 combined oxygen | |

(6) DETAILED DESCRIPTION

The present inventors have extensively investigated surface treatment methods which were conventionally reported and at the same time given attention to the phenomenon of surface treatment. Intensive researches have been conducted on the irradiation of ultraviolet rays which generate ozone by the oxidation of oxygen in the air. As a result, it has been found that the irradiation of ultraviolet rays from a low pressure mercury lamp on the basis of the principle of ozone oxidation has an effect on reducing the contact angle of synthetic resin surface with an aqueous solution and a stably hydrophilic surface can also be obtained. Thus the present invention has been completed.

The present invention will hereinafter be described in detail by reference to the figures.

Figure 2:
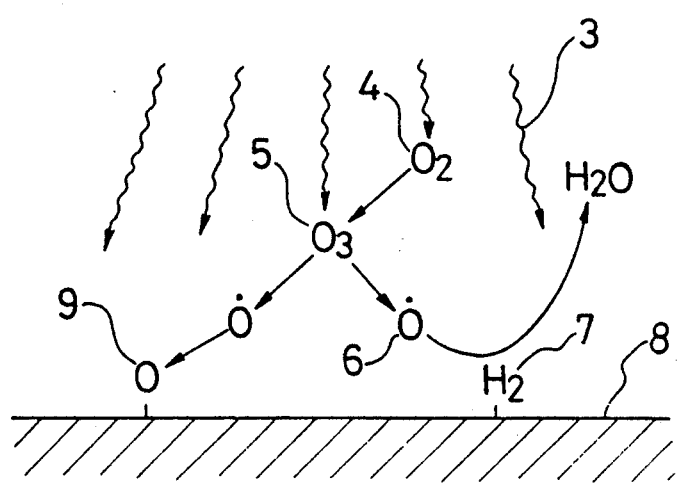
FIG. 2 illustrates the principle of hydrophilication treatment in this invention.

FIG. 1 illustrates an example of the method for conducting the hydrophilication treatment of synthetic resin surface in this invention. FIG. 2 illustrates the principle of hydrophilication treatment in this invention. A molded article 1 prepared by molding the resin to a shape suitable for application is irradiated with ultraviolet rays 3 from the ultraviolet lamp 2. Ozone 5 is evolved from oxygen 4 in the air around the molded article. Ozone 5 further generates its radical, that is, activated oxygen 6 by the irradiation of ultraviolet rays to ozone 5. The activated oxygen 6 has a strong oxidizing property and combines with hydrogen 7 which contributes to the hydrophobic property of the resin. The activated oxygen 6 removes hydrogen 7 from the resin surface 8 to render the resin surface 8 hydrophilic and at the same time further enhances the hydrophilic property by forming the combination 9 with the resin surface itself. The surface is also plated and propagated with cells.

The method for the hydrophilication treatment of this invention is capable of hydrophilicating most resins such as thermoplastic resin and thermosetting resin. The thermoplastic resin includes, for example, polystyrene resin, polyacrylate resin, polyvinyl chloride resin, polycarbonate resin, polyamide resin, ABS resin, polysulfone resin and polyfluorocarbon resin. Examples of thermosetting resin include polyurethane resin, epoxy resin and cellulose resin. Thermoplastic resin and thermosetting resin can of course be used singly or in combination of two or more.

The ultraviolet rays generally have a wave length of 184.9 nm for generating ozone from oxygen and a wave length of 253.7 nm for converting ozone to activated oxygen. The most effective low pressure mercury lamp was found to actually generate large quantity of the ultraviolet rays having these wave lengths. High pressure and ultrahigh pressure mercury lamps were also found to be effective.

Therefore in the practice of this invention, the radiation source irradiating ultraviolet rays is generally somewhat effective whereas the low pressure mercury lamp, a rich radiation source of aforesaid wave length, is effective in particular.

In order to increase the hydrophilication grade of the resin surface 8, that is, to lower the contact angle with water, it is required to extend the irradiation time of ultraviolet rays or to increase the output of the ultraviolet lamp. These means lead to increase in resin temperature and, in some types of the resin used, result in deformation of shape due to temperature rise. The deformation of resin may be avoided by carrying out pulse irradiation of ultraviolet rays instead of continuous irradiation. Furthermore the pulse irradiation of ultraviolet rays is capable of enhancing the hydrophilication grade of the resin surface 8 with scarcely accompanying thermal deformation of the vessels and ultraviolet ray degradatiuon of the resin interior.

The hydrophilicated vessels thus obtained can be effectively used as culture devices or inspection apparatus.

Several preferred embodiments are described in the following examples to illustrate the invention.

EXAMPLE 1

A low pressure mercury lamp (ORC Manufacturing Co., Ltd., 65 watt) was located at a distance of 25 mm from the surface of various synthetic resin plates and irradiated these plates for 5 minutes. The contact angles of these plates with water were measured before and after irradiation. The results are illustrated in Table 1.

TABLE 1

| Synthetic resin | Contact angle (degree) | |
| --- | --- | --- |
| | Before irradiation | After irradiation |
| Polystyrene | 95 | 9 |
| Polyacrylate | 75 | 10 |
| Polyamide | 97 | 12 |
| Polyvinyl chloride | 87 | 10 |

EXAMPLE 2

(1) Treatment of dish

Polystyrene dishes were injection molded without using a mold releasing agent.

The same low pressure mercury lamp as in Example 1 was located at a distance of 25 mm from the bottom surface of the dish thus obtained, irradiated the dish for 5 minutes and the contact angle was measured. After obtaining the contact angle of 10 degrees or less, the dish was closed with a lid and sterilized with ethylene oxide. After sterilization, the dish was allowed to stand at 60° C. for a week in order to remove residual ethylene oxide gas.

(2) Preparation of Cells

HeLa cells, e.g. adhesion dependent cells, were subcultured to propagate cells to such an extent that cells became visible on the bottom surface of a Roux jar. The resulting HeLa cells were inoculated in Eagle's MEM medium containing 10% of calf serum in a glass Roux jar and cultured at 37° C. in an incubator. The adhered cells were dispersed into the medium as single cells and used for subculture.

(3) Cultivation test of adhesion dependent cells in the aforesaid dish irradiated with ultraviolet rays.

A dish treated in (1) was charged with which had been added in sterile condition sterilized MEM medium to its 10% of calf serum and inoculated with HeLa cells prepared in (1). Stationary culture was carried out at 37° C. in an incubator. The adhesion dependent cells were observed their extent of adhesion and compared with those of the glass Roux jar and those of the polystyrene dish of (1) without irradiation treatment of ultraviolet rays. As a result, cells were similarly adhered and grown on the bottom parts of the glass Roux jar and the polystyrene dish irradiated with ultraviolet rays.

On the other hand, cells were scarcely adhered and grown on the bottom part of the polystyrene dish without irradiation treatment. Only a few cells were found in suspension.

EXAMPLE 3

(1) Treatment of dish

A low pressure mercury lamp (15 watt) was located at a distance of 25 mm from a polystyrene dish having a diameter of 90 mm, irradiated the dish for 5 minutes and the contact angle was measured. After obtaining 30 degrees or less in the contact angle with water, the dish was closed with a lid and sterilized with ethylene oxide gas to obtain a treated dish.

(2) Preparation of medium

A cotton stuffed Erlenmeyer flash was charged with 1% agar medium and sterilized in an autoclave.

(3) Charge test of medium in the dish

The medium prepared in (2) was maintained at about 50° C. and charged in the irradiated dish obtained in (1) and the untreated dish in such quantity as illustrated in Table 2 respectively. The extended areas of the medium in these dishes were observed and the results are illustrated in Table 2.

TABLE 2

| Quantity charged (cc) | Irradiated dish | Untreated dish |
| --- | --- | --- |
| 8.5 | Δ | X |
| 9.0 | Δ | X |
| 9.5 | O | X |
| 10.0 | ◉ | X |
| 10.5 | ◉ | Δ |
| 11.0 | ◉ | Δ |
| 11.5 | ◉ | O |

Note,
X: Medium is extended on about ⅔ of the bottom area only.
Δ: Medium is extended on about 4/5 of the bottom area only.
O: Medium is extended over the whole area of bottom after good shaking.
◉: Medium is easily extended over the whole area of bottom.

EXAMPLE 4

Polystyrene dishes were injection molded without using a mold releasing agent. A low pressure mercury lamp (Japan Storage Battery Co., Ltd., 250 watt) was located at a distance of 15 mm from the bottom surface of the dish. Ultraviolet rays were irradiated for a given time continuously or by pulses and relationships between irradiation time and contact angles were measured. The results are illustrated in Table 3. When ultraviolet rays were continuously irradiated for 60 seconds or more, the dish was deformed by heat. On the other hand, no thermal deformation of the dish was observed even though overall irradiation in excess of 300 seconds was carried out by pulses.

In addition, the same effect was obtained on the hydrophilication of dish surface as clearly illustrated by the contact angles, even if ultraviolet rays were irradiated continuously or by pulses.

TABLE 3

| Overall irradiation time (sec) | Contact Angle (σ) | |
| --- | --- | --- |
| | Continuous irradiation | Pulse irradiation* |
| 0 | 95 | 95 |
| 30 | 55 | 55 |
| 60 | 24 | 24 |
| 90 | 14 | 15 |
| 120 | 9 | 9 |
| 150 | 9 | 9 |
| 180 | 9 | 9 |

*Pulse irradiation means that irradiation having a pulse length of 30 seconds was repeated with a pulse spacing of 60 seconds.

EXAMPLE 5

(1) Treatment of dish

The same low pressure mercury lamp as in Example 4 was located at a distance of 15 mm from the bottom surface of a polystyrene dish which was previously injection molded without using a mold releasing agent. Ultraviolet rays were irradiated 4 pulses having a pulse length of 30 seconds and a pulse spacing of 60 seconds to measure the contact angle. The contact angle of 9 degrees was obtained on the resulting dish. The resulting dish was closed with a lid, sterilized with ethylene oxide gas and then allowed to stand at 60° C. for a week in order to remove residual ethylene oxide gas.

(2) Preparation of cells

HeLa cells, e.g. adhesion dependent cells, were subcultured to propagate cells to such an extent that cells became visible on the bottom surface of a Roux jar. The resulting HeLa cells were inoculated in Eagle's MEM medium containing 10% of calf serum in a glass Roux jar and cultured at 37° C. in an incubator. The adhered cells were dispersed into the medium as single cells and used for subculture.

(3) Cultivation test of adhesion dependent cells in the aforesaid dish irradiated with ultraviolet rays.

A dish treated in (1) was charged with which had been added in sterile condition sterilized MEM medium to its 10% of calf serum and inoculated with HeLa cells prepared in (1). Stationary culture was carried out at 37° C. in an incubator. The adhesion dependent cells were observed their extent of adhesion and compared with those of the glass Roux jar and those of the polystyrene dish of (1) without irradiation treatment of ultraviolet rays. As a result, cells were similarly adhered and grown on the bottom parts of the glass Roux jar and the polystyrene dish irradiated with ultraviolet rays. On the other hand, cells were scarcely adhered and grown on the bottom part of the polystyrene dish without irradiation treatment. Only a few cells were found in suspension.

EXAMPLE 6

(1) Treatment of dish

The same low pressure mercury lamp as in Example 4 was located at a distance of 15 mm from the bottom surface of a polystyrene dish which was previously injection molded without using a mold releasing agent and had a diameter of 90 mm. Ultraviolet rays were irradiated 2 pulses having a pulse length of 30 seconds and a pulse spacing of 60 seconds to measure the contact angle. The contact angle of 24 degrees was obtained on the resulting dish. The resulting dish was closed with a lid and sterilized with ethylene oxide to prepare a treated dish.

(2) Preparation of medium

A cotton stuffed Erlenmeyer flask was charged with 1% agar medium and sterilized in an autoclave.

(3) Charge test of medium in the dish

A given quantity of the medium prepared in (2) was maintained at about 50° C. and charged in the irradiated dish obtained in (1) and the untreated dish. The extended area of the medium in the dish was observed and the results are illustrated in Table 4.

As plastic dishes are generally hydrophobic, sometimes the medium does not extend well over the whole area of these dishes in poured plate culture or multiple layer culture. Therefore larger amount of the medium must be charged and the medium is sometimes wasted. The amount of medium can be reduced by lowering the contact angle of dish surface with matter.

TABLE 4

| Quantity charged (cc) | Irradiated dish | Untreated dish |
| --- | --- | --- |
| 8.5 | Δ | X |
| 9.0 | Δ | X |
| 9.5 | O | X |
| 10.0 | ◉ | X |
| 10.5 | ◉ | Δ |
| 11.0 | ◉ | Δ |

TABLE 4-continued

| Quantity charged (cc) | Irradiated dish | Untreated dish |
| --- | --- | --- |
| 11.5 | ◉ | ○ |

Note,
X: Medium is extended on about ⅔ of the bottom area only.
Δ: Medium is extended on about 4/5 of the bottom area only.
○: Medium is extended over the whole area of bottom after good shaking.
◉: Medium is easily extended over the whole area of bottom.

As mentioned above, the method of this invention has following advantages for the hydrophilication treatment of synthetic resin.
1. Equipment for the treatment is inexpensive.
2. Procedure is simple because the treatment is a dry process.
3. Continuous treatment can be carried out.
4. Hydrophilic surface obtained is uniform.

Besides the method for the hydrophilication treatment of synthetic resin in this invention may be applied to various articles. The articles which may be easily employed for the hydrophilication include, for example, surfaces of tissue culture vessels represented by dishes and bottles; plastic inspection apparatus such as slide and cover glasses and micropipettes; general purpose measuring vessels such as ordinary pipettes and diluter tips; and the like. These articles are mentioned to illustrate this invention and not to limit the scope of the present invention.

Furthermore in Examples, the advantages of lowering the contact angle with water were illustrated by using the dishes as examples. The effect may be briefly divided under the following three items.
(I) The adhesion dependent cells can proceed their adhesive growth by reduction of the contact angle and increase in the hydrophilicity due to ultraviolet irradiation.
(II) The aqueous solution can be more easily charged into the vessels by lowering the contact angle, although the hydrophilicity is not so high as to proceed adhesive growth of the adhesion dependent cells.
(III) The hydrophilication of dishes has advantages that high viscosity medium becomes easy to pour and necessary amount of the medium can be reduced. Besides the easy pouring leads to the reduction of time required for testing a large number of bacteria.

The dishes were mentioned as an example of (I). Concerning the culture devices of cells, however, a group of trays generally called microtrays can also be used for the adhesive growth of cells depending upon the irradiation conditions. In addition, aside from the adhesive growth, the present invention can be applied to the trays for the analysis of hemocyte elements such as HLA typing trays (Iwasaki tray), micro trays for platelet typing and the like. Furthermore, this invention can be used for mass culture apparatus, for example, cultivation systems using multiplate, multidisc, multiple trays or hollow fibers.

Although the dishes were illustrated as an example of II), the inspection apparatus wherein the hydrophilicity is to be provided are not limited to the dishes. The inspection apparatus include, for example, microtray groups, pipettes, test tubes, spits tubes and microscopic plates for urinary precipitate test, and the like.

Plastic slide and cover glasses may also be prepared easily by using the treatment method of this invention.

The inspection apparatus termed in the claims of this invention also include those which are used by putting an aqueous solution dropwise on a plate.

The accuracy of measurement is decreased when the foams contained in the solution adhere to the internal surface of pipettes, and micropipettes in particular. Therefore the treatment of this invention is effective for settling the problem. This invention is also effective for the liquid measuring apparatus such as general purpose pipettes, diluter tips, etc.

Possibility for industrial application

The hydrophilication treatment on the surface of synthetic resin object can be easily, inexpensively and uniformly treated by the method of this invention.

The present invention has eliminated the traditional problems by providing the inexpensive culture devices or inspection apparatus having the stably hydrophilic surface without adverse effect on the tissue, microorganisms or inspection. Such culture devices or inspection apparatus are formed of synthetic resin and at least a part of their surface are subjected to the oxidation treatment by the irradiation of ultraviolet rays and particularly by the pulse irradiation.

Furthermore the present invention has provided the method for manufacturing the culture devices and inspection apparatus which are capable of being continuously produced with an inexpensive equipment for treatment, easy to manufacture, uniformly treated and inexpensive. Consequently this invention has enabled us to prepare the culture devices or inspection apparatus which are formed of synthetic resin and at least a part of their surface are subjected to the oxidation treatment by irradiating ultraviolet rays.

What is claimed is:

1. A method for reducing the contact angle of a synthetic resin object to be contacted with an aqueous liquid, comprising: irradiating the surface of a synthetic resin object, having a first contact angle with water, with ultraviolet rays having wavelengths of 184.9 nm and 253.7 nm, without irradiating so as to cause the shape of the surface of said synthetic resin object to change, whereby the surface of said synthetic resin object is oxidized by said irradiation to obtain a synthetic resin object having an oxidized surface with a second contact angle with water, wherein said synthetic resin is selected from the group consisting of thermoplastic and thermosetting resins and said second contact angle with water is less than said first contact angle.

2. The method of claim 1, wherein said irradiating with ultraviolet rays is conducted by pulse irradiation.

3. The method of claim 2, wherein said synthetic resin object is in the form of a culture device or inspection apparatus.

4. The method of claim 1, wherein said synthetic resin object is in the form of a culture device or inspection apparatus.

5. A method as claimed in one of claims 1-2, wherein the contact angle with water is not more than 30°.

* * * * *